United States Patent [19]

Mead et al.

[11] 3,996,786

[45] Dec. 14, 1976

[54] MEANS FOR ON-LINE DETERMINATION OF BOILING POINT PROPERTIES OF CRUDE OIL

[75] Inventors: Theodore C. Mead, Port Arthur; Charles W. Harrison, Nederland; Irene W. Kwan, Houston, all of Tex.

[73] Assignee: Texaco Inc., New York, N.Y.

[22] Filed: Dec. 29, 1975

[21] Appl. No.: 644,500

[52] U.S. Cl. .................................. 73/17 A; 73/53
[51] Int. Cl.$^2$ .................................... G01N 25/08
[58] Field of Search ........... 73/17 A, 53, 61.3, 61.1

[56] References Cited
UNITED STATES PATENTS

| | | | |
|---|---|---|---|
| 3,239,432 | 3/1966 | Rhodes et al. | 73/53 |
| 3,253,454 | 5/1966 | Neil | 73/17 |
| 3,720,096 | 3/1973 | Woodle | 73/53 |

Primary Examiner—Herbert Goldstein
Attorney, Agent, or Firm—T. H. Whaley; C. G. Ries; Ronald G. Gillespie

[57] ABSTRACT

On-line sensors sense the kinematic viscosity, the infrared absorption, at a predetermined wavelength, the ultraviolet absorption of a predetermined wavelength, and the sulfur content of crude oil and corresponding signals are provided to a computer circuit. The computer circuit solves the equation:

$$M\%BP = \{-C_1 + C_2[\ln(IR \times C_3)] + C_4[\ln UV] - C_5 S - C_6[\ln(IR \times C_3)](\ln UV) + C_7[\ln(IR \times C_3)]S\} \ln KV$$

where M%BP is a particular percent boiling point property of crude oil, IR is the infrared absorption of the crude oil, S is the sulfur content of the crude oil, KV is the kinematic viscosity of the crude oil, UV is the ultraviolet absorption of the crude oil and $C_1$ through $C_7$ are constants.

6 Claims, 1 Drawing Figure

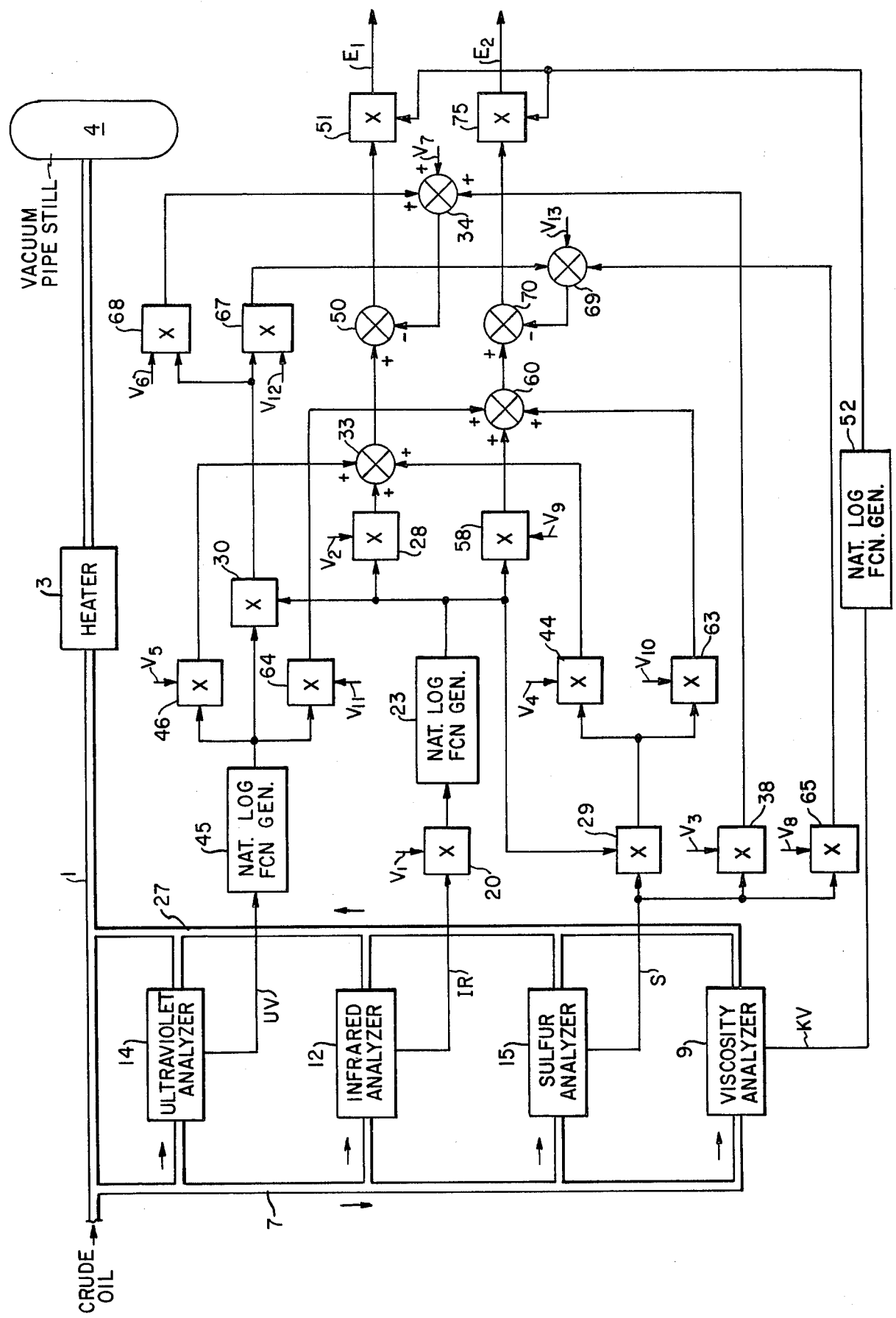

MEANS FOR ON-LINE DETERMINATION OF BOILING POINT PROPERTIES OF CRUDE OIL

BACKGROUND OF THE INVENTION

1. Field of the Invention

The present invention relates to metering systems in general and, more particularly, to systems for determining boiling point properties of crude oil.

2. Description of the Prior Art

Heretofore boiling point properties of crude oil were determined by distillation tests which required samples to be taken and removed to a laboratory for determination. The present system differs by utilizing an empirically derived equation using four parameters of crude oil which may be analyzed on line so that an on-line boiling point determination can be made.

SUMMARY OF THE INVENTION

An on-line boiling point analyzer which provides a signal corresponding to a particular boiling point property of crude oil flowing in a line, includes analyzers sampling the crude oil and providing signals corresponding to the sulfur content, to the infrared absorption at a predetermined wavelength, to the ultraviolet absorption at another predetermined wavelength, and to the kinematic viscosity of the crude oil. A circuit provides the signal corresponding to the particular boiling point property of the crude oil in accordance with the signals from the analyzer.

The objects and advantages of the invention will appear more fully hereinafter, from a consideration of the detailed description which follows, taken together with the accompanying drawing wherein one embodiment is illustrated by way of example. It is to be expressly understood, however, that the drawing is for illustrative purposes only and is not to be construed as defining the limits of the invention.

DESCRIPTION OF THE DRAWING

The FIGURE shows crude oil being fed into a vacuum pipe still, shown in partial schematic form, being monitored by an on-line boiling point analyzer, constructed in accordance with the present invention, shown in block diagram form.

DESCRIPTION OF THE INVENTION

The following empirically derived equation may be utilized to determine a particular boiling point of crude oil:

$$M\%BP = \{-C_1 + C_2[\ln(IR \times C_3)] + C_4(\ln UV) - C_5 - S - C_6[\ln(IR \times C_3)](\ln UV) + C_7(IR \times C_3)]S\} \ln KV \quad (Eq. 1)$$

where M%BP is a particular percent boiling point property, such as the 30% boiling point or the 50% boiling point, IR is the infrared absorption of the crude oil at a predetermined wavelength, S is the sulfur content of the crude oil, KV is the kinematic viscosity of the crude oil, UV is the ultraviolet absorption of the crude oil at a predetermined wavelength, and $C_1$ through $C_7$ are constants.

The particular percent boiling point to be determined by equation 1 is governed by the values of $C_1$ through $C_7$. The following Table relates the 30 and 50% boiling points to the values of the constants $C_1$ through $C_7$.

|       | 30 % BP    | 50 % BP    |
|-------|------------|------------|
| $C_1$ | 1745.4246  | 3926.6512  |
| $C_2$ | 525.6163   | 1129.0759  |
| $C_3$ | 1000       | 1000       |
| $C_4$ | 254.8026   | 541.8975   |
| $C_5$ | 144.6291   | 278.5749   |
| $C_6$ | 65.6417    | 141.0175   |
| $C_7$ | 30.2110    | 69.0106    |

Referring now to FIG. 1, crude oil is being fed in a line 1 through a heater 3 to a vacuum pipe still 4. It is desirable in the operation of the vacuum pipe still 4 to know the boiling point properties of the crude oil in line 1. Samples are continually drawn off to line 7 and applied to a viscosity analyzer 9, an infrared analyzer 12, an ultraviolet analyzer 14 and a sulfur analyzer 15 which returns the samples through line 27 to line 1. Viscosity analyzer 9, infrared analyzer 12, ultraviolet analyzer 14, and sulfur analyzer 15 provide signal KV, corresponding to the kinematic viscosity of the crude oil corrected to 100° F, signal IR, corresponding to the infrared absorption of the crude oil at 6.27 microns, signal UV corresponding to the ultraviolet absorption of the crude oil at 269 microns, and signal S, corresponding to the sulfur content of the crude oil, respectively.

A source of direct current voltages (not shown) provides direct current voltages $V_1$ through $V_{13}$. Voltage $V_1$, corresponding to the term $C_3$ in equation 1, is multiplied with signal IR by a multiplier 20 to provide a signal to a conventional type natural log function generator 23. Function generator 23 provides a signal, corresponding to the term $\ln(IR \times C_3)$ to multipliers 28, 29. Multiplier 28 multiplies the signal from function generator 23 with the direct current voltage $V_2$, corresponding to the 30% boiling point constant 525.6163 ($C_2$ in equation 1) to provide a signal to summing means 33.

A multiplier 38 multiplies signal S with voltage $V_3$, corresponding to the 30% boiling point constant 144.6291 ($C_5$ in equation 1) to provide a signal to summing means 34.

Multiplier 29 multiplies the signal from function generator 23 with signal S to provide a signal, corresponding to $[\ln(IR \times C_3)]S$, to a multiplier 44. Multiplier 44 multiplies the signal from multiplier 29 with voltage $V_4$, corresponding to the 30% boiling point constant 30.2110 ($C_7$ in equation 1), to provide a product signal to a summing means 33.

Ultraviolet analyzer 14 provides signal UV to a natural log function generator 45 which provides a signal corresponding to $\ln(UV)$. A multiplier 46 multiplies the signal from generator 45 with voltage $V_5$, corresponding to the 30% boiling point constant 254.8026 ($C_4$ in equation 1) to provide a signal. Summing means 33 sums the signals from multipliers 28, 44 and 46, in effect summing the positive terms of equation 1, to provide a signal.

Multiplier 30 multiplies the signals from function generators 23, 45 to provide a signal to a multiplier 48 where it is multiplied with voltage $V_6$. Voltage $V_6$ corresponds to the 30% boiling point constant 65.6417 ($C_6$ in equation 1).

Summing means 34 in effect sums all the negative terms in equation 1 when it sums the signals from multipliers 38, 48 with voltage $V_7$, corresponding to the 30% boiling point constant 1745.4246 ($C_1$ in equation 1). Subtracting means 50 subtracts the signal provided by summing means 33 from the signal provided by summing means 33 to provide a signal to a multiplier 51. Signal KV from viscosity analyzer is applied to a natural log function generator 52 which provides a signal corresponding to the term lnKV in equation 1. Multiplier 51 multiplies the signals from function generator 52 and subtracting means 51 to provide signal $E_1$ corresponding to 30% boiling point of the crude oil in line 1.

A signal $E_2$, corresponding to the 50% boiling point of the crude oil, is also provided as follows. Signal S from sulfur analyzer 15 is multiplied with voltage $V_8$, corresponding to the 50% boiling point constant 278.5749 ($C_5$ in equation 1), by a multiplier 65 to provide a product signal. The signal from function generator 23 is multiplied with voltage $V_9$, corresponding to the 50% boiling point constant 1129.0759 ($C_2$ in equation 1), by a multiplier 58 to provide a product signal to summing means 60.

The product signal from multiplier 29, corresponding to the term [ln(IR×$C_3$)]S, is applied to a multiplier 63 where it is multiplied with voltage $V_{10}$, corresponding to the 50% boiling point constant 69.0106 ($C_7$ in equation 1). A multiplier 64 multiplies the signal from function generator 45 with voltage $V_{11}$, corresponding to the 50% boiling point constant 541.8975 ($C_4$ in equation 1) to provide a signal. Summing means 60 sums the signals provided by multipliers 58, 63 and 64, to provide a sum signal.

Multipliers 65, 67 multiply signal S and the signal from multiplier 30, respectively, with voltages $V_8$ and $V_{12}$, respectively, to provide product signals to summing means 69 where they are summed with voltage $V_{13}$ to provide a sum signal. Voltages $V_{12}$, $V_{13}$ correspond to the 50% boiling point constants 141.0175 and 3926.6512, respectively ($C_6$ and $C_1$, respectively, in equation 1). Summing means 69 effectively sums the negative terms of equation 1. Subtracting means 70 subtracts the signal provided by summing means 69 from the signal provided by summing means 60 to provide a signal to a multiplier 75. Multiplier 75 multiplies the signal from subtracting means 70 with the signal from function generator 52 to provide signal $E_2$ corresponding to the 50% boiling point of the crude oil in line 1.

The systems hereinbefore described provide an on-line determination of at least one boiling point property of crude oil. It can provide as many boiling point properties simultaneously as desired.

What is claimed is:

1. A boiling point analyzer for on-line determination of at least one boiling point property of crude oil flowing in a line comprising means for sampling the crude oil and providing samples, viscosity analyzing means receiving samples of the crude oil and providing a signal KV corresponding to the kinematic viscosity of the crude oil, infrared analyzing means connected to the sampling means and receiving a sample for providing a signal IR corresponding to the infrared absorption of the crude oil at a predetermined wavelength, ultraviolet analyzing means connected to the sampling means and receiving a sample for providing a signal UV corresponding to the ultraviolet absorption of the crude oil at another predetermined wavelength, sulfur analyzing means connected to the sampling means and receiving a sample for providing a signal S corresponding to the sulfur content of the crude oil, and boiling point signal means connected to all the analyzing means for providing a boiling point signal corresponding to a boiling point property of the crude oil.

2. A boiling point analyzer as described in claim 1 in which the boiling point signal means provides the boiling point signal in accordance with the following equation:

$$M\%BP = \{-C_1 + C_2[\ln(IR \times C_3)] + C_4[\ln UV] - C_5 S - C_6[\ln(IR \times C_3)][\ln UV] + C_7[\ln(IR \times C_3)]S\} \ln KV$$

where M%BP is a particular boiling point property of the crude oil, IR is the infrared absorption of the crude oil at the one predetermined wavelength, UV is the ultraviolet absorption of the crude oil at another predetermined wavelength, S is the sulfur content of the crude oil, KV is the kinematic viscosity of the crude oil, and $C_1$ through $C_7$ are constants.

3. A boiling point analyzer as described in claim 2 in which M%BP is the 30% boiling point and the constants $C_1$ through $C_7$ have the values of 1745.4246, 525.6163, 1000, 254.8026, 144.6291, 65.6417 and 30.2110, respectively.

4. A boiling point analyzer as described in claim 2 in which M%BP is the 50% boiling point and the constants $C_1$ through $C_7$ have values of 3926.6512, 1129.0759, 1000, 541.8975, 278.5749, 141.0175 and 69.0106, respectively.

5. A boiling point analyzer as described in claim 2 further comprises second boiling point signal means for providing a second boiling point signal corresponding to a second boiling point property of the crude oil in accordance with the equation and in which the constants $C_1$ through $C_7$ have one set of values for the first boiling point property and another set of values for the second boiling point property.

6. A boiling point analyzer described in claim 5 in which one of the boiling point signal means provides a signal corresponding to the 30% boiling point of the crude oil as its boiling point signal in accordance with the equation where the constants $C_1$ through $C_7$ have values of 1745.4246, 525.6163, 1000, 254.8026, 144.6291, 65.6417 and 30.2110, respectively, and the other boiling point signal means provides a signal corresponding to the 50% boiling point as its boiling point signal in accordance with the equation where $C_1$ through $C_7$ have values of 3926.6512, 1129.0759, 1000, 541.8975, 278.5749, 141.0175 and 69.0106, respectively.

* * * * *